US010341555B2

(12) United States Patent
Menon et al.

(10) Patent No.: US 10,341,555 B2
(45) Date of Patent: Jul. 2, 2019

(54) CHARACTERIZATION OF A PHYSICAL OBJECT BASED ON ITS SURFACE ROUGHNESS

(71) Applicants: Naresh Menon, Pasadena, CA (US); Gregory Howard Bearman, Pasadena, CA (US); Leonard Nelson, Pasadena, CA (US)

(72) Inventors: Naresh Menon, Pasadena, CA (US); Gregory Howard Bearman, Pasadena, CA (US); Leonard Nelson, Pasadena, CA (US)

(73) Assignee: Chromologic LLC, Monrovia, CA (US)

( * ) Notice: Subject to any disclaimer, the term of this patent is extended or adjusted under 35 U.S.C. 154(b) by 1175 days.

(21) Appl. No.: 13/573,868

(22) Filed: Oct. 10, 2012

(65) Prior Publication Data

US 2015/0264254 A1    Sep. 17, 2015
US 2017/0099434 A9    Apr. 6, 2017

Related U.S. Application Data

(60) Provisional application No. 61/630,127, filed on Dec. 2, 2011.

(51) Int. Cl.
*H04N 5/232* (2006.01)
*H04N 5/225* (2006.01)
*G01N 21/47* (2006.01)

(52) U.S. Cl.
CPC ....... *H04N 5/23222* (2013.01); *H04N 5/2256* (2013.01); *G01N 21/4738* (2013.01)

(58) Field of Classification Search
None
See application file for complete search history.

(56) References Cited

U.S. PATENT DOCUMENTS

| 5,379,352 A * | 1/1995 | Sirat ............... G06K 9/6247 |
| | | 382/276 |
| 7,853,792 B2 | 12/2010 | Cowburn |
| 2002/0039184 A1 * | 4/2002 | Sandusky ............ G01J 3/02 |
| | | 356/369 |

(Continued)

OTHER PUBLICATIONS

Article, Fingerprinting documents and packaging, Brief Communications, Nature, vol. 436, Jul. 28, 2005 and Supplementary Methods, 5 pages.

*Primary Examiner* — Michael J Hess
(74) *Attorney, Agent, or Firm* — Lewis Roca Rothgerber Christie LLP

(57) ABSTRACT

The present invention is directed to a method and apparatus that involves improved characterization of an object based on its surface roughness and other unique features without having to necessarily define a fixed and predetermined region of interest. In accordance with one aspect, the present invention provides a method for characterizing an object based on a pattern of the object's surface roughness. The method comprises the steps of obtaining a unique image of a feature on the surface of the object, converting the image obtained into certain electrical signals and processing the electrical signals so they are associated with the object and thereby provide a characterization of the object that is used to generate a unique identifying signature for the object.

19 Claims, 7 Drawing Sheets

(56) References Cited

U.S. PATENT DOCUMENTS

| | | | |
|---|---|---|---|
| 2004/0032581 A1* | 2/2004 | Nikoonahad | G01N 21/55 356/237.2 |
| 2004/0207836 A1* | 10/2004 | Chhibber | G01N 21/4738 356/237.4 |
| 2005/0123186 A1* | 6/2005 | Reeves et al. | 382/141 |
| 2007/0233404 A1* | 10/2007 | Lally | G01N 21/95607 702/35 |
| 2008/0219503 A1 | 9/2008 | Di Venuto et al. | |
| 2008/0225298 A1* | 9/2008 | Fairley et al. | 356/445 |
| 2009/0002688 A1* | 1/2009 | Soeda et al. | 356/73 |
| 2009/0213120 A1* | 8/2009 | Nisper | G01J 3/504 345/426 |
| 2010/0158377 A1* | 6/2010 | Cowburn et al. | 382/181 |
| 2011/0096955 A1 | 4/2011 | Voloshynovskiy et al. | |
| 2012/0013899 A1* | 1/2012 | Amanullah | G01N 21/9501 356/237.5 |
| 2012/0275681 A1* | 11/2012 | Honda | C12M 33/00 382/133 |
| 2013/0116812 A1* | 5/2013 | Drasek | G01B 11/0608 700/103 |

\* cited by examiner

CHARACTERIZATION OF A PHYSICAL OBJECT BASED ON ITS SURFACE ROUGHNESS

This application is a non-provisional patent application claiming priority to U.S. provisional patent application No. 61/630,127 filed on Dec. 2, 2011 entitled "IMPROVED CHARACTERIZATION OF PHYSICAL ITEM".

STATEMENT REGARDING FEDERALLY SPONSORED RESEARCH OR DEVELOPMENT

This invention was made with government support under contract number W911NF-09-0050 awarded by the U.S. Army Research Office. The government has certain rights in the invention.

FIELD OF THE DISCLOSURE

The present disclosure relates to a device and process for characterization of a physical item.

DEFINITION OF TERMS USED IN THE DISCLOSURE

The term "electrical signals" used hereinafter in this disclosure refers to, but not limited to, analog signals, digital signals, electronic signals, electronic data and the like, used in any electrical/electronic system.

The term "image" used hereinafter in this disclosure refers to, but not limited to, digital image, optical image, hologram, X-Ray image, and the like.

The term "object" used hereinafter in this disclosure refers to, but not limited to, any physical item, material, part, component or any other item with a visible surface.

These definitions are in addition to those expressed in the art.

BACKGROUND

Unique features found on living-beings have been used for many years to characterize living-beings for identification. For example, fingerprints have long been used as a unique characteristic of each person for identification purposes. Other known methods of characterizing persons based on the same general principle involve voice pattern recognition, DNA testing and various other unique physical characteristics of human beings.

For physical items, unique features can be used to identify or characterize the physical item. Any manufacturing process for any physical item typically involves a sequence of process steps, such as chemical, mechanical, electrical or thermal. During the manufacturing process, these steps, based on the machinery and operating parameters, can create unique random minute surface features for each manufactured physical item. Such surface features cannot be replicated, controlled or eliminated under manufacturing conditions that may not use the exact same equipment or the exact same process steps and its defined parameters. Small variations can create different minute surface features that are unique from physical item to physical item.

Because random surface features, such as abrasion location, a particular surface roughness and the like, of a given material are unique, attempts have been made to capture various features as an intrinsic fingerprint to uniquely identify a particular object. Under this approach, a number of different systems and methods were attempted to detect unique intrinsic features of objects for determination of their authenticity. However, those systems have been unreliable, and unsuccessful. These methods have significant limitations, are difficult to implement and prone to false detections.

Pattern recognition of unique intrinsic features has been used in the past as an approach to identify objects. Under this approach, a number of different systems and methods were attempted to detect unique intrinsic features of objects for determination of their authenticity. In U.S. Patent Application US2010/0158377 ("'377 disclosure"), characterization of materials like paper and plastics by generating signatures based on natural structured texture of the materials' surfaces is discussed.

The '377 disclosure discloses the use of laser light focused on an object's surface, the laser light reflected and collected to obtain information about the object's surface roughness. Although the information collected can then be processed to generate a unique identifying signature for the material, this process is significantly limiting and constrained because it requires not only the use of laser light, but also imaging of the same region of interest on each object, i.e. the imaging area has to be pre-selected for later comparison. It is necessary to use the same region of interest because different regions of interest on the given material's surface have different random patterns of microstructure encoded by detected speckle patterns, so the same region of interest must be compared for identification purpose. As well, the wavelength of the light used must be adjusted to match the expected feature size on the object. As a result multiple wavelengths of the light are required to work on different types of objects. These constraints mandate specialized efforts in orienting a pre-selected region of interest of an object and in adjusting illumination configurations and wavelength for different types of objects.

In U.S. Pat. No. 7,853,792 ("'792 patent"), a speckle pattern detection method is disclosed. The '792 patent describes that the micro topology of carton and paper using a coherent light source such as a laser beam is used for object authentication. However, the '792 patent is limited to speckle pattern detections of materials made of paper or cardboard. In addition, the use of a laser requires special equipment and efforts that are costly.

In U.S. Patent Application US 2008/0219503 ("'503 disclosure"), a fingerprint for a given material can be generated by reading the random pattern of microstructure of the material on a defined region of interest. The '503 disclosure characterizes the material by acquiring an image of the material containing noise characteristics through illuminating the region of interest with diffused or specular light. The '503 disclosure requires special tailoring, i.e. varying resolutions of imaging for different classes of materials with different microstructure feature sizes, and special effort in orienting the region of interest. Moreover, the '503 disclosure also requires the region of interest to match some specific mathematical requirements to minimize false detections.

U.S. Patent Application US2011/0096955 attempts to resolve the issue of resolution, when using imaging devices with low resolution capacity for detecting counterfeits, by attaching macrolenses to a material's surface to enhance the resolution of microstructure of the surface. However, macrolenses for this purpose require additional components that increase the costs.

Diffuse lighting is common illumination approach, in which the light comes from many angles. Portraiture, macrophotography and outdoor scenes usually look best with diffuse lighting. However, for the purpose of characterizing objects via surface features, diffuse lighting produces a more uniform and smaller range of data values with reduced contrast that smooth out spatial structure. The prior art characterization devices and methods that use diffuse lighting do so because it tends to have a more uniform illumination, but such use suffers from the lack of data values with reduced contrast and is therefore unreliable.

Prior methods and devices for characterization of a given object employ extracting and evaluating natural randomness of the microstructure of an object's surface. To increase reliability special types of illumination are required. Certain defined regions of interest to be imaged and compared must be identified and pre-defined. Because of the varying microstructure feature size of the surface of different objects, special efforts in tailoring imagining configurations, such as wavelength of the light, resolution of imaging device or macrolenses, are required. Precise orientation of the region of interest is also required for comparison. Given these constraints, the prior art devices and methods are difficult to calibrate, difficult to implement and prone to false detections.

SUMMARY

The present invention is directed to a method and apparatus that involves improved characterization of an object based on its surface roughness and other unique features without having to necessarily define a fixed and predetermined region of interest. In accordance with one aspect, the present invention provides a method for characterizing an object based on a pattern of the object's surface roughness. The method comprises the steps of obtaining a unique image of a feature on the surface of the object, converting the image obtained into certain electrical signals and processing the electrical signals so they are associated with the object and thereby provide a characterization of the object that is used to generate a unique identifying signature for the object.

In accordance with one embodiment, the surface of the object is illuminated by focusing light from at least one light source, in a predetermined direction and angle onto a feature on the surface of the object. Upon striking the object, the light is reflected and scattered from the surface of the object. The light scattered and reflected by the surface is then intercepted and an image is captured that can be used to uniquely identify the object, based on the characterization of the focused light and the direction and angle of illumination, which comprises a pattern representing uniquely, for example, the surface feature and other information of the object. Typically, the reflected and scattered light is intercepted as an image by at least one camera. The image is then converted into electrical signals that are used for processing information, including spatial information, defined by the light reflected and scattered by the surface, and its direction and angle, to obtain unique identifying features of the object. These electrical signals are linked to the object and identify the object for characterizing the object.

A 2D imaging sensor can be used to capture the image of an object and then the image is converted into electrical signals. The electrical signals may be stored as data for later defining the object by its captured characteristics, and this stored data may be kept in one of a local or remote repository.

The unique identifying features captured in the stored data may be compared with corresponding features of a reference.

In accordance with another aspect, the present invention provides an apparatus for characterizing an object. The apparatus comprises at least one light source, an imaging device, a rectangular platform for placing the object, and a back plate, all enclosed in a tube housing. The light source is operable to generate and focus light onto a feature on the surface of the object at a fixed angle. The imaging device is located above the object at a predetermined focal distance and is operable to intercept at least a portion of the light reflected and scattered by the surface of the object to capture a pattern representing at least one feature of the object, and convert the image into electrical signals. The apparatus further comprises at least one processing device to process the electrical signals into data that provides unique identifying features of the object, and links the object with the data created from the electrical signals for characterizing the object.

The light source comprises point light sources such as LED, Laser and X-Ray. Additionally, the light source comprises extended light sources such as LEDs. Additionally, the light source comprises Incandescent lamp or Electroluminescent lamp. Generally, a range of coherent or incoherent light sources can be used.

Typically, the imager in the imaging device comprises a 2D image sensor, Additionally, the 2D image sensor comprises at least one of a color and a panchromatic sensor. The imaging device further comprises at least one camera.

The processing device comprises at least one microprocessor. Additionally, the apparatus further comprises at least one of a local repository and a remote repository for storing the electrical signals.

BRIEF DESCRIPTION OF ACCOMPANYING DRAWINGS

The disclosure will now be explained in relation to the accompanying drawings, in which.

DETAILED DESCRIPTION OF ACCOMPANYING DRAWINGS

Figure 1:
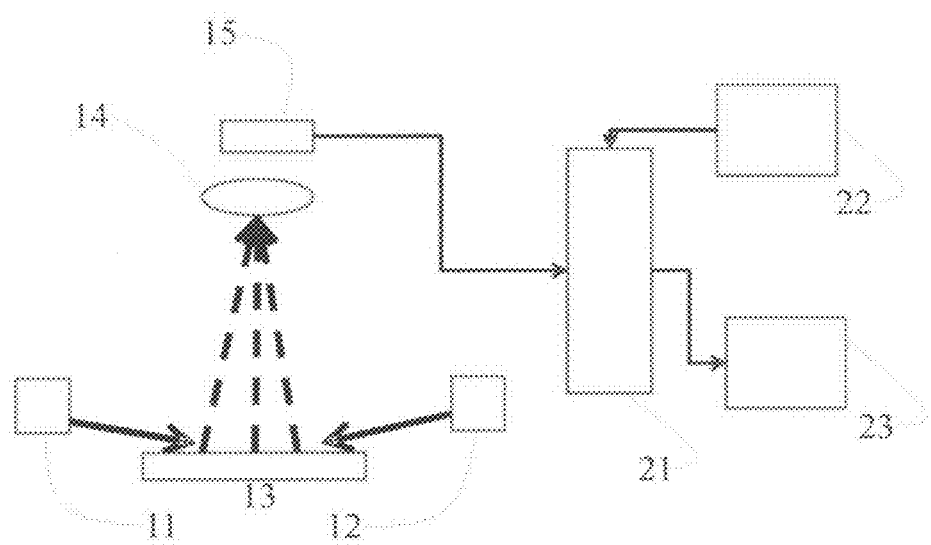
FIG. 1 illustrates a schematic view of the apparatus for characterization of an object in accordance with the present disclosure.

The invention will now be described with reference to the embodiments shown in the accompanying drawings. The embodiments do not limit the scope and ambit of the invention. The description relates purely to the exemplary preferred embodiments of the disclosed structure, the process of the present invention, and its suggested applications.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The description herein after, of the specific embodiments will so fully reveal the general nature of the embodiments herein that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

A detailed description of the preferred embodiments of the present invention teaches illuminating an object by focusing light from a light source, and capturing the light reflected from the object as unique data for comparison to reference data for a similar object. Since most physical items do not themselves emit visible light but reflect incident natural sunlight and artificial light, illuminating the object for surface characterization is important.

A 2D image texture under predetermined illumination of rough surfaces can provide information about the surface geometry of an object on micro scales. Such information can then be analyzed and classified to accurately characterize an object or a class of objects.

Many opportunities and methodologies for creating duplicate and counterfeit objects exist. The manufacturing of duplicates or counterfeits typically creates objects that may appear to be the same as the original, but likely have their own unique identifying features such as scratches or other types of groves or unique markings caused by the manufacturing process.

For the present invention the surface of an object is illuminated by focusing light from at least one light source, in a predetermined direction onto a feature on the surface of the object. Light can be provided by either a point or an extended light source. An extended light source provides light that cannot be focused to a point by lens, mirrors or pinholes. When a rough surface is illuminated by a light beam bundle from a directional light, surface topology creates shadows and contrast whereas diffuse lighting washes them out. The effect of directional illumination is to provide higher feature contrast and more dynamic range in the image.

Light source of sufficient illumination to illuminate the object under inspection (20) is used. In accordance with a preferred embodiment, raking lighting is used. In raking lighting, light is emitted by the light source at grazing angles of approximately twenty degrees (20°) or less. Raking lighting enhances surface features significantly by providing shadows that are washed out by diffuse lighting. The enhancement is a function of the illumination angle, with weaker enhancement at higher angles.

Figure 5:
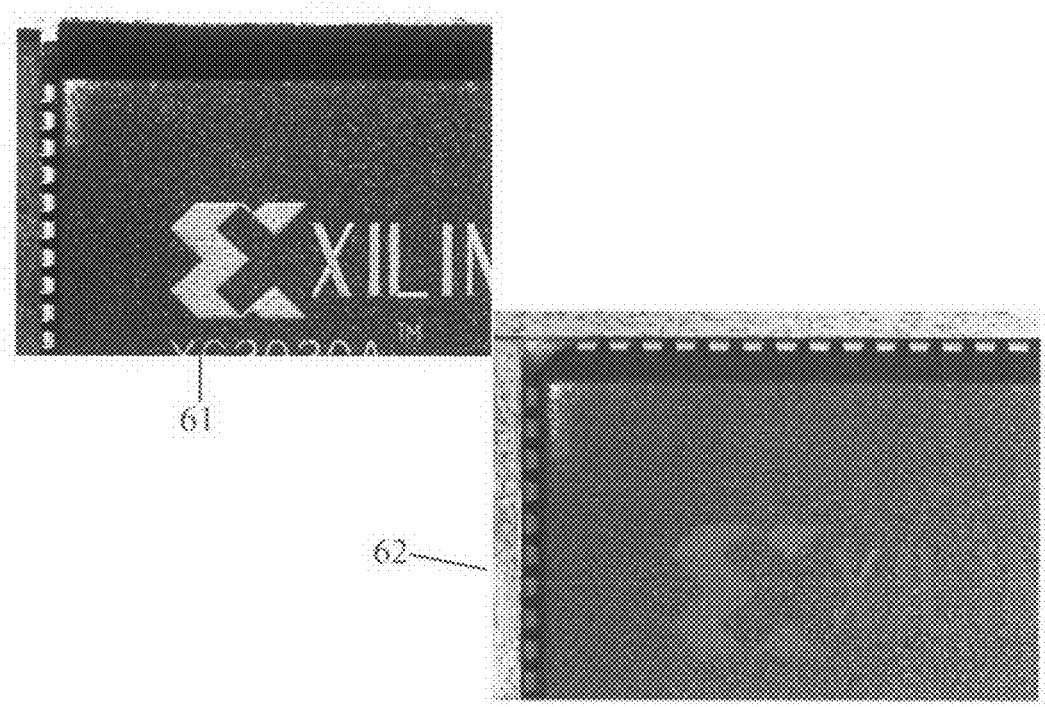
FIG. 5 illustrates a digital image of an object obtained from the apparatus and the 2-D Fourier transform of the image following edge correction in accordance with an embodiment of the present disclosure.
Figure 6:
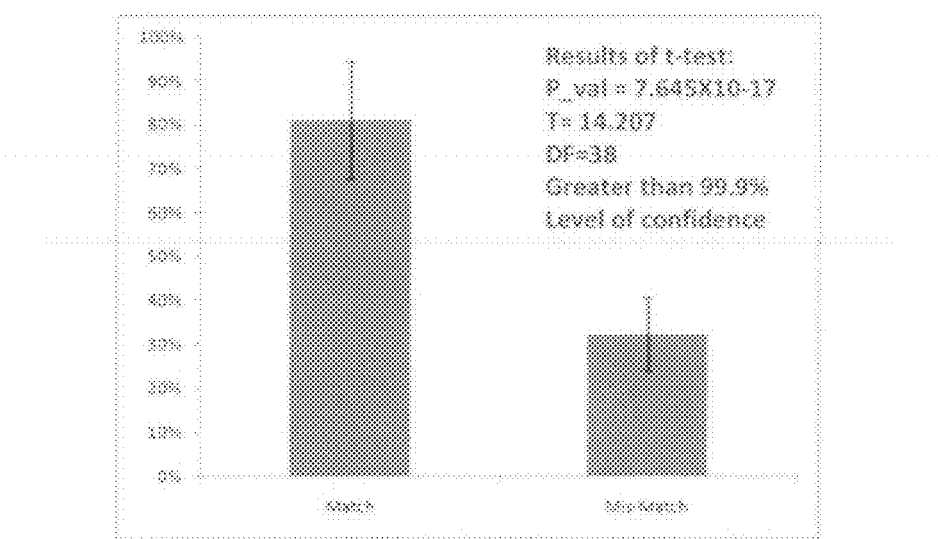
FIG. 6 illustrates a graphical representation of the data from the apparatus processed by the method in accordance with FIG. 3, for twenty objects.
Figure 7:
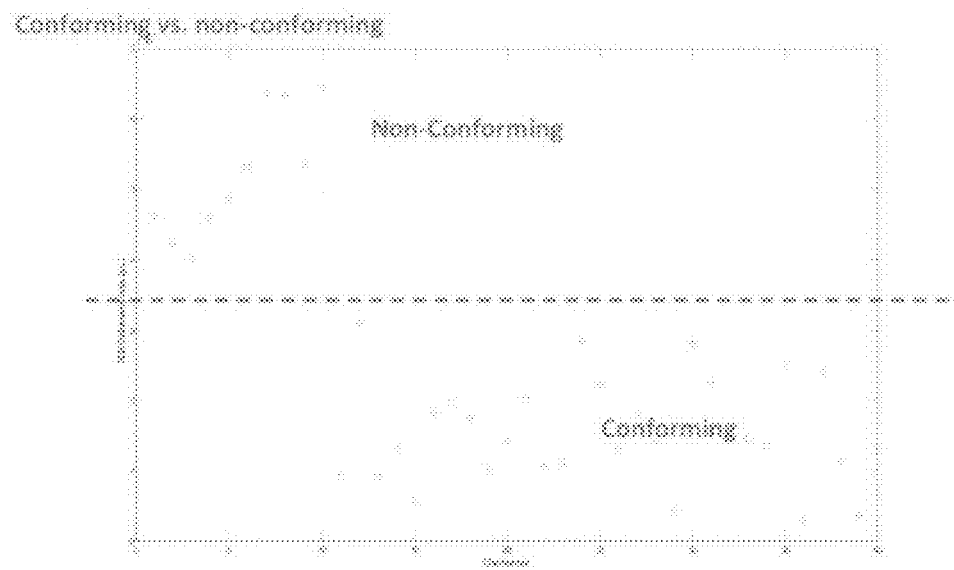
FIG. 7 illustrates a graphical representation of the data from the apparatus processed by the method in accordance with FIG. 4, for twenty objects.

Light enhancement for the purpose of characterizing the object can be used to provide more surface topographical information from 2D image texture. Raking lighting provides larger contrast and accentuating smaller surface features through shadowing and higher contrast. FIG. 5 shows a comparison of two images of the surface of a microchip. Image (61) was obtained under illumination conditions, according to the teachings of the present invention, using lighting provided at a grazing angle and image (62) was obtained without using a grazing angle. The difference of the amount of surface features captured is shown. The raking lighting image provides much more topological surface information than the non-raking lighting image. This difference is significant and can even be observed using only the human eye.

The enhanced method of characterizing an object according to the present disclosure uses raking light. An illustration of the apparatus for implementing a preferred embodiment of this method is shown schematically in FIG. 1. One or more light sources, here shown as light sources (11) and (12) are providing illumination to the object that is being characterized (20) by striking the object with one or more light sources at fixed angles for each light source. Here, the fixed angle is the same for each light source, and is approximately twenty degrees (20°). The light beam emitted by the light sources is reflected and scattered in many directions according to the law of reflection upon meeting the rough surface of the object under inspection (20). The incidental light beam at the grazing angle significantly enhances surface features by providing shadows and contrast that otherwise would not be observed. A signal collection and imaging optics (14) is placed directly above the object under inspection (20) at a focal distance appropriate to capture an optical image of the object under inspection (20). The imaging optics (14) enables a portion of the light reflected by the surface of the object to be intercepted in order to obtain an image containing uniquely identifying features and other optical information. This image is composed of a combination of the light reflected and scattered by the surface of the object and contains information about locations of features, shadows, and any differences in the material, scratches, or other anomalies that may exist on the surface of the object, based on refractive indices, size and location of microscopic surface features, edge of the object, natural optical absorption, as well as its optical activity. A 2D imaging sensor (15), either a color or panchromatic (B/W) sensor, can be connected to the imaging optics (14). By using the 2D imaging sensor (15), computer readable electronic signals make up the optical image, and containing the uniquely identifying features embodying surface topography and materials of the object under inspection (20) can be obtained. These electrical signals are then processed into identifying data that is defined by the optical image obtained, by sending them to a processor (21) capable of processing the electrical signals into identifying data for characterization of the object and comparison to other data that identifies a reference. In accordance with an embodiment, these electrical signals are converted into identifying vectors that can be used to characterize the object under inspection. Further, it is possible to store the identifying characteristic information about the object under inspection at a remote location (22) as a reference for later comparison to information regarding other objects. A user interface (23) can be used to inform the user of conformance or traceability after comparison.

The present invention discloses a device that implements the method of capturing the uniquely identifying information of an object. In a first step (step 1) of the method according to the present invention, the object under inspection (20) (not shown) is placed on a platform (13) as shown in FIG. 1. One or more light sources, here shown as two light sources (11) and (12), which can be, in accordance with a preferred embodiment, raking lights, illuminate the object under inspection (20) from a fixed angle approximately equal to or less than twenty degrees (20°). The precise orientation and area or areas on the object under inspection (20) to be viewed are not critical in step 1 because the inventive illumination method enables capturing of sufficient unique surface features to determine the characterization of the object under inspection (20) through spatial relationships rather than through mere recognition of the orientation and positioning of any particular surface feature. In a second step (step 2), the uniquely identifying information of one or more intrinsic surface features of the object under inspection (20) can be obtained in a form of an optical image under the described conditions for illumination in step 1 by intercepting the reflected and scattered light from one or more light sources (11) and (12). In a third step (step 3), the electrical signals embodying the intrinsic surface features can be acquired by converting the image obtained in step 2 for further processing and manipulation. It is not necessary for the object under inspection (20) to undergo any particular treatment, marking or tagging. The object under inspection (20) retains and maintains its original condition from the manufacturing process.

The electrical signals embodying the images are converted into unique data files containing surface topological information of the object under inspection (20). This may subsequently be processed by a processor or processors (21) capable of extracting identifying characteristic pattern(s) of the object from the electrical signals in a fourth step (step 4). The extracted characteristic pattern(s) of the object under inspection (20) can then be stored as a unique data file on a remote or local database system (22). Further data processing can be done to compare the data for the object under inspection (20) to reference data. The uniquely identifying information from the images can be compared to a reference to authenticate the object under inspection (20) to similar uniquely identifying information for a reference object that has previously been inspected according to the method described in the present invention. For such a comparison, the reference object under inspection (20) should initially be subjected to the same method for examination that the target object under inspection (20) will undergo. To have a reliable comparison, the illumination and interception conditions as those used for obtaining the reference characteristic should be the same as those for the target object used in step 1 and step 2. Through the same digitizing of step 3 and processing of step 4, a characteristic pattern of the reference and the object under inspection (20) can then be obtained. The obtained uniquely identifying information of the object under inspection (20) can be compared with the reference uniquely identifying information by means of known image processing methods with an interface (23) that provides information of the conformance between the two objects that have been inspected (20). A matching level between the uniquely identifying information reference object and the object under inspection (20) can be determined from further processing, either through automated computing or visual inspecting, including that for the probability of identity or lack of identity between the two objects.

Figure 2:
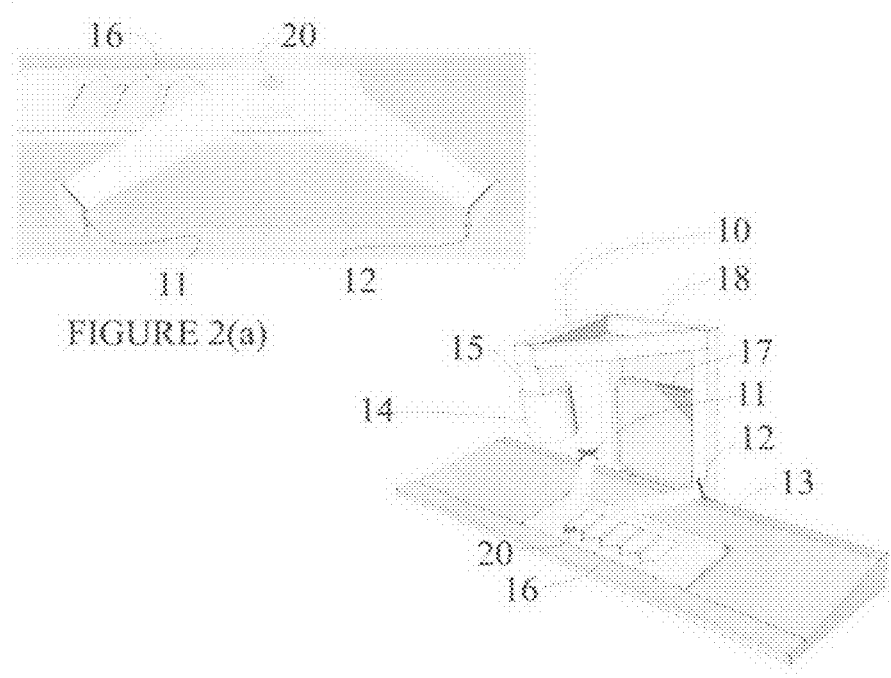
FIG. 2(a) illustrates a schematic representation showing components of the apparatus in accordance with an embodiment of the present disclosure.
FIG. 2(b) illustrates a schematic representation showing components of the apparatus in accordance with an embodiment of the present disclosure.
Figure 3:
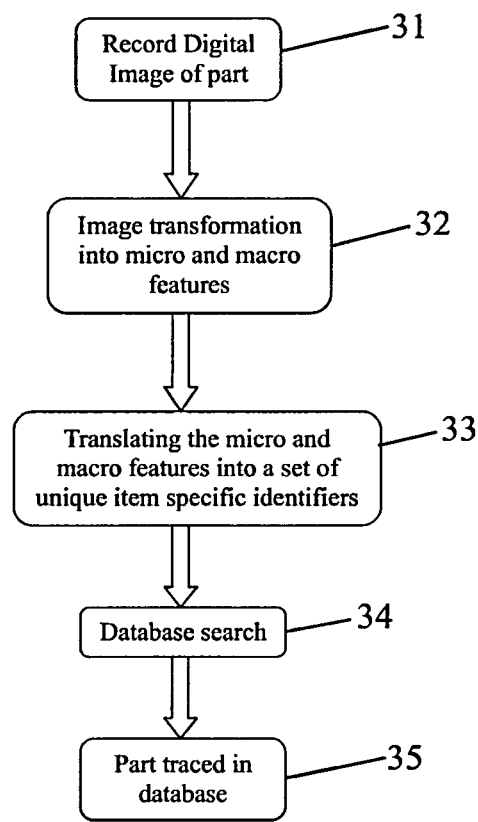
FIG. 3 illustrates a flowchart for a method for tracing an object, in accordance with an embodiment of the present disclosure.

Referring to FIGS. 2(a) and 2(b), a schematic representation showing components of the apparatus in accordance with an embodiment of the present invention, is illustrated. The apparatus is generally identified by the reference number (10). The apparatus (10) enables objects to be viewed at a microscopic level to have uniquely identifying information manifested by the minute random roughness formed during manufacturing of the object. As shown in FIG. 3, an object under inspection (20) is placed on a rectangular viewing platform (13). In accordance with one embodiment, the viewing platform (13) can have a gradually elevated shape with the back end slightly higher than the front end at approximately fifteen degree (15°) angle. At least one light source is used.

In accordance with one embodiment the light sources (11) and (12) comprise multiple LED sources rated for an optical output. In a preferred embodiment, twelve (12) LEDs per bank with two banks can be used. White light LEDs are used for this purpose.

The light sources (11) and (12) are preferably raking light sources and each are arranged to have the same angle with respect to the tilted surface of the object under inspection (20), providing the grazing angle to which the apparatus (10) is calibrated. At the center of the viewing platform is a viewing area, which can be rectangular in shape and large enough to place the object under inspection (20) upon it. To fully illuminate and strike the object under inspection (20) with light, the two light sources (11) and (12) are mounted on each side of the back plate (19) located at the center of the back end of the viewing platform (19). FIG. 2(a) shows a top view of this lighting arrangement. In FIG. 2, the two light sources (11) and (12) are fixed at a right angle at an imaginary intersection of the fixtures of the two sources (11) and (12). In some embodiments, a ring light source may be used. This physical arrangement provides for illuminating the entire object under inspection (20) with each light source comprising an array of LEDs that emit light beams, as shown in FIG. 2. The light beam emitted by the light sources (11) and (12) are reflected and scattered in many directions, according to the law of reflection, from the rough surface of the object under inspection (20). The incidental light beam from each of the light sources (11) and (12) are at a grazing angle that significantly enhances surface features of the object under inspection (20) by providing shadows and contrast that otherwise would not be observed. To intercept the reflected and scattered light, signal collection and imaging optics (14) is connected with a 2D imaging sensor (15), mounted on the front tip of a triangle support (18), positioned directly over the object under inspection (20) at a focal distance. The imaging optics (14) enables a portion of the light reflected by the surface of the object under inspection (20) to be intercepted in order to obtain an image of the surface features of the object under inspection (20). This image is composed of a combination of the light reflected and scattered by the surface of the object under inspection (20) based on, for example, its refractive index, size and location of microscopic surface features, edge of the object, natural optical absorption, material, as well as its optical activity. The 2D imaging sensor (15), which may be a color or panchromatic (black and white), enables the conversion of the image having the uniquely identifying features and information to computer readable electrical signals embodying the uniquely identifying features and information. A computer system may be connected to this apparatus (10) to process the electrical signals into data files in order to obtain the uniquely identifying information of the object under inspection (20).

In accordance with other embodiments of the disclosure, polarization analysis of the surface of the object under inspection (20) using incoherent or coherent light is performed with substantially the same optical source and receiver arrangement, but with the addition of polarization modulating optical components in the illumination and image detection path to quickly and accurately measure polarization dependence of the microscopic image of the surface of the object under inspection (20).

Referring to FIG. 3, a flowchart for a method for tracing an object, in accordance with an embodiment of the present disclosure is illustrated. The method comprises the following steps,

- recording the digital image of the object under inspection (31). In a preferred embodiment, an 8 mega-pixel 2D image of a feature on the surface of the object under inspection is captured by raking light.
- Transforming the image into micro and macro features (32). In a preferred embodiment the image is then processed with an edge correction method to trim the transition of the object from its surroundings, digitally transformed by a 2D Fourier transform into a 512×512 matrix.
- Translating the micro and macro features into a set of unique object specific identifiers (33). The principal components of the image may be extracted from the vector that forms the diagonal of the 2D Fourier transform matrix by using the 21st through the 100th terms.
- Searching the data base. A cross-correlation analysis may be used, wherein the principal components of the captured image features are compared to values available in a repository.
- Tracing the object in the data base. Based on the cross-correlation value, the object's unique data file may be tracked and identified in a database. Its conformance to known characteristics of a class of objects can also be determined.

Figure 4:
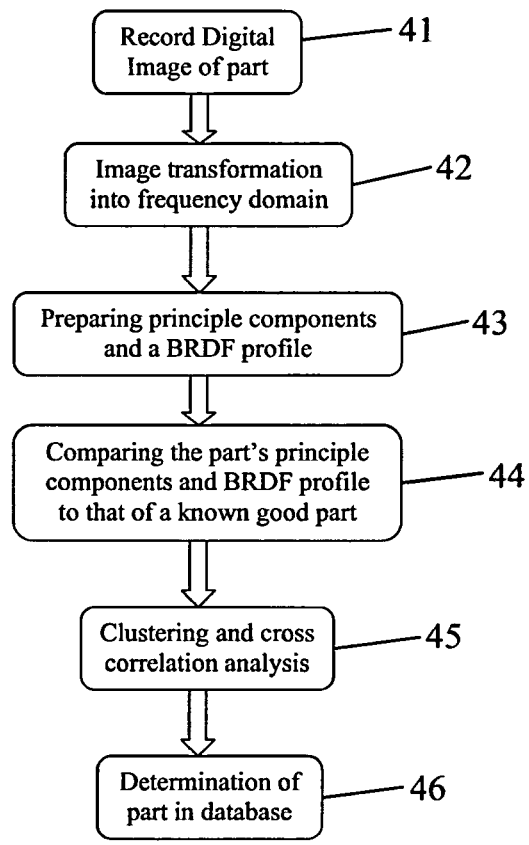
FIG. 4 illustrates a flowchart for a method for determining the conformance of an object to acceptable parameters, in accordance with an embodiment of the present disclosure.

Referring to FIG. 4, a flowchart for a method for determining the conformance of an object to acceptable parameters, in accordance with an embodiment of the present disclosure is illustrated. The method comprises the following steps,

- Recording the digital image of the object under inspection (41). In a preferred embodiment an 8 mega-pixel 2D image of a feature on the surface of the object under inspection is captured using a raking light source.
- Transforming the image into frequency domain (42). The image may be processed and digitally transformed by a 2D Fourier transform into a 512×512 matrix.
- Preparing the principal components and a Bidirectional Reflectance Distribution Function (BRDF) profile (43). The principal components of the unique image file can be extracted from the vector that forms the diagonal of the 2D Fourier transform matrix by using the 21st through the 100th terms and a BRDF profile can be created to characterize the reflection properties of the surface of the object under inspection.
- Comparing the principle components and the BRDF profile to that of a known reference object data file (44). The principal components of the image and the BRDF profile are compared to values available in a database having a reference object that has previously been inspected.
- Clustering and cross correlation analysis (45)—A cross-correlation analysis is performed on the compared values.
- Determination of object conformance (46)—Based on the cross-correlation value, the object is tracked and identified in a database. Based on the value of the correlation value, its conformance to known characteristics of a class of objects is also determined.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements, as the use may be in one of the embodiments to achieve one or more of the desired objects or results.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

What is claimed is:

1. A method for characterizing an object, said method comprising:
   - striking a surface of the object with light from at least two incoherent light sources, each incoherent light source oriented to simultaneously generate incoherent raking light onto a feature on a surface of the object at grazing angles of twenty degrees or less relative to the surface of the object, wherein the at least two incoherent light sources face the surface of the object such that the incoherent light travels directly to the surface of the object, wherein the at least two incoherent light sources are spaced apart such that the at least two incoherent light sources shine light onto the object from different directions;
   - obtaining a digital image of micro features on the surface of the object;
   - converting said image into electrical signals comprising micro surface features based on spatial relationships of multiple surface features; and
   - processing said signals into unique identifying reference information for characterizing the object; and
   - comparing the unique identifying reference information to corresponding features of a reference.

2. The method as claimed in claim 1, wherein converting said image further comprises converting said image into electrical signals by at least one 2D imaging sensor.

3. The method as claimed in claim 1, wherein processing said signals further comprises performing a Fourier Transform on said signals to link the object with said signals for characterizing the object.

4. The method as claimed in claim 1, wherein the method further comprises storing said signals on at least one of a local repository and a remote repository.

5. An apparatus for characterizing an object, said apparatus comprising:
- at least two incoherent light sources, each incoherent light source oriented to simultaneously generate incoherent raking light onto a feature on a surface of the object at grazing angles of twenty degrees or less relative to the surface of the object, wherein the at least two incoherent light sources face the surface of the object such that the incoherent light travels directly to the surface of the object, wherein the at least two incoherent light sources are spaced apart such that the at least two incoherent light sources shine light onto the object from different directions;
- at least one imaging device located above the object at a predetermined focal distance, said imaging device adapted to intercept at least one portion of the light reflected and scattered by said surface;
- said imaging device further adapted to capture an optical image comprising a pattern representing at least one feature of the object;
- said imaging device further adapted to convert said image into electrical signals; and
- at least one processing device adapted to process said electrical signals to link the object with said signals for characterizing the object by comparison to stored reference data.

6. The apparatus as claimed in claim 5, wherein said at least two light sources are a point light source or an extended light source.

7. The apparatus of claim 5, wherein the apparatus comprises only light sources oriented at grazing angles of twenty degrees or less relative to the surface of the object.

8. The apparatus as claimed in claim 5, wherein said at least two light sources are an LED, an X-ray, an incandescent lamp, or an electroluminescent lamp.

9. The apparatus as claimed in claim 5, wherein said imaging device further comprises at least one 2D image sensor, said at least one 2D image sensor comprising at least one of a color sensor and a panchromatic sensor.

10. The apparatus as claimed in claim 5, wherein said apparatus further comprises at least one of a local repository and a remote repository.

11. The apparatus as claimed in claim 5, wherein said apparatus further comprises a rectangular viewing platform for placing the object, said platform having a gradually elevated shape with a first end slightly higher than an opposite second end.

12. An apparatus for characterizing an object based on intrinsic properties of the object, the apparatus comprising:
- a first incoherent raking light source and a second incoherent raking light source, wherein the first and second raking light sources are each configured to simultaneously direct incoherent light at a grazing angle towards a surface of an object, wherein the grazing angle is an angle of twenty degrees or less relative to the surface, and wherein the incoherent light sources face the surface of the object such that the light is configured to travel directly from the incoherent light sources to the surface of the object, wherein the first and second incoherent light sources are spaced apart such that the first and second incoherent light sources shine light onto the object from different directions, and wherein the apparatus comprises only light sources oriented at grazing angles of twenty degrees or less relative to the surface of the object; and
- an imaging device located aligned with the surface of the object at a predetermined focal distance, wherein the imaging device obtains a digital image of the surface of the object, and wherein the digital image comprises microscopic level details of the surface of the object made visible by the light from the raking light source having been reflected and scattered by the surface of the object due to physical properties of the surface of the object.

13. The apparatus of claim 12, wherein the first and second raking light sources are oriented at a same angle with respect to the surface of the object.

14. The apparatus of claim 12, wherein the digital image is stored in a memory associated with the imaging device.

15. The apparatus of claim 12, wherein the imaging device is configured to obtain a digital image of a surface roughness of the object.

16. The apparatus of claim 14, further comprising an electronic storage remote from the imaging device.

17. The apparatus of claim 12, wherein at least one digital image of a sample object is configured to be compared with at least one digital image of a reference object.

18. The apparatus of claim 17, wherein the digital image of the reference object is configured to be stored at a remote location and the digital image of the sample object is configured to be stored at a location local to the imaging device.

19. The apparatus of claim 17, further comprising a user interface configured to inform a user of conformance or traceability after comparison of the at least one digital image of the sample object with the digital image of the reference object.

* * * * *